United States Patent [19]

Wang

[11] Patent Number: 5,444,530

[45] Date of Patent: Aug. 22, 1995

[54] WEATHER IDENTIFIER AND VISIBILITY SENSOR

[75] Inventor: Ting-I Wang, Gaithersburg, Md.

[73] Assignee: Scientific Technology, Inc., Gaithersburg, Md.

[21] Appl. No.: 72,385

[22] Filed: Jun. 7, 1993

[51] Int. Cl.⁶ .......................................... G01N 21/00
[52] U.S. Cl. ................................ 356/338; 250/573; 250/574; 356/73; 356/438
[58] Field of Search ............... 356/73, 337, 338, 438, 356/442; 250/573, 574, 575; 340/601, 602

[56] References Cited

U.S. PATENT DOCUMENTS 4,240,752 12/1980 Tausch et al. ..................... 250/574
4,760,272 7/1988 Wang ................................. 250/573

OTHER PUBLICATIONS

Point Visibility Meter: A forward scatter instrument for the measurement of aerosol extinction coefficient by J. V. Winstanley and M. J. Adams.
An Optical Rain Gauge Based on Forward Scattering by L. G. Kazovsky, Senior member, IEEE.
Journal of Applied Meterology vol. 17: A Feasibility Study of Identifying Weather By Laser Forward Scattering by K. B. Earnshaw et al.
Journal of Applied Meteorology vol. 21 No. 11, Nov. 1982; Laser Weather Identifier: Present and Future by Ting-I Wang et al.
HHS, Inc. HHS-TD-083 Jun. 1982 VR-301 Visibility Meter, Technical Data Sheets.

Primary Examiner—Richard A. Rosenberger
Assistant Examiner—Robert Kim
Attorney, Agent, or Firm—Charles H. Thomas

[57] ABSTRACT

A weather identification system is provided which employs a first photosensitive receiver positioned directly in the path of a beam of light a predetermined distance from a partially coherent light beam source. The first photosensitive receiver is in direct optical communication with the light beam source to produce electronic signals in response to scintillations caused by particle movement between the source and the first receiver. Signals from the detected scintillations are filtered to provide an output having a frequency range above one kilohertz indicative of rain intensity, and a second output having a frequency range lower than two hundred fifty hertz indicative of snow intensity. A second photosensitive receiver is positioned out of the path of the beam of light and is oriented at an oblique angle relative thereto to provide an output indicative of forward scattering of light from scintillations that occur in the beam of light. The signals from the second photosensitive receiver provide an output having a signal strength characteristic of visibility. The weather identification system thereby senses precipitation, categorizes the precipitation as either rain or snow, and measures visibility. The weather condition indicating system is ideal for use in remotely monitoring airfields.

5 Claims, 4 Drawing Sheets

WEATHER IDENTIFIER AND VISIBILITY SENSOR

BACKGROUND OF THE INVENTION

1. Field of the Invention

The present invention relates to a system for optically and electronically ascertaining the existence and nature of precipitation and for measuring visibility in the. ambient air from a remote location.

2. Description of the Prior Art

A light emitting diode weather identification system has previously been developed to remotely detect the existence of precipitation and to determine the nature of precipitation. That is, the prior weather identification system can differentiate between rain and snow. This prior weather identification system was established with the intent of automating surface weather observations at airports. The ability to completely automate surface observations is critically dependent on the ability to automatically distinguish between rain and snow. This prior system is disclosed in U.S. Pat. No. 4,760,272 issued on Jul. 26, 1988.

The prior weather identification system is able to correctly identify different types of precipitation in a near field region by transmitting a partially coherent light source over a path length much shorter than that of prior optical precipitation systems. According to the system of U.S. Pat. No. 4,760,272 a partially coherent light source, such as an infrared light emitting diode, may be used in place of a laser source which conventional optical weather identification systems previously required. The partially coherent beam of light is transmitted over a short distance of less then one meter and is detected by an optical receiver located in communication with the transmitter and in spaced separation therefrom.

The percentage light intensity fluctuations (scintillation indices) detected by the optical receiver within certain frequency ranges are indicative both of the existence of precipitation and the nature of the detected precipitation. Frequency components above one kilohertz are indicative of rain. Snow induced frequencies are primarily at a few hundred hertz. Accordingly, electronic signals generated from the received scintillations are directed to at least two different band pass filters to quantify scintillations in low arid high frequency ranges. Scintillation signals in the low frequency range indicate snow while scintillations in the higher frequency range indicate rain. The low frequency band may be from twenty five hertz to two hundred fifty hertz, for example, while the high frequency band may extend from one kilohertz to four kilohertz.

Because high frequency components of rain drop induced scintillations are critical for discriminating between rain and snow, a half angle of incoherency which is too large may result in an insufficient number of usable signals in the high frequency band. Therefore, for all practical purposes the product of one half the angle of incoherency of the transmitter, as measured in radians, multiplied by the distance of the transmitter and receiver, must be no greater than about 2.5 millimeters.

While the system of U.S. Pat. No. 4,760,272 quite accurately determines the level and nature of precipitation, it does not provide an indication of visibility level. As a result of increasingly acute environmental problems, a need exists for accurate sensors to measure optical visibility in the atmosphere.

A number of prior visibility sensors have been devised and are available commercially. These conventional visibility sensors are of three general types. These are: (1) transmissometer instruments; (2) backscatter instruments, and (3) forwardscatter instruments. For more than thirty years the system used most widely to assess visibility has been the Federal Aviation Administration (FAA) runway visual range (RVR) transmissometer. This system uses a field sensor placed adjacent to the runway and measures the atmospheric transmission of a fixed seventy five meter path. A major problem with the RVR transmissometer, however, is its limited dynamic range. A well maintained transmissometer can only provide accurate visual ranges from one half its baseline to ten times its baseline (a factor of twenty). In addition, the absolute calibration for the transmissometer demands frequent field maintenance and may be contaminated by background light such as daylight and street lights. The lengthy baseline of seventy five meters that is required causes another problem for large scale field deployment. Due to these disadvantages, the use of a transmissometer as part of an automated weather station for unattended operation is impractical.

Backscatter visibility sensor instruments operate on the principle that the extinction coefficient may be related to the intensity of light scattered back from an object. Sources of error for these instruments arise from the uncertainty of the empirical relationship between the back scattering coefficient and visibility, and from the failure to allow for optical extinction between the instrument and the scattering volume. However, the major problem for field operation of such backscatter instruments is the contamination of reflected signals by rain and snow. These ambiguities prevent backscatter visibility sensors from providing reliable measurements of visibility during precipitation.

Forwardscatter instruments operate on the assumption that light scattered at certain angles in the forward direction can be related to the extinction coefficient. Forwardscatter instruments are less sensitive to precipitation contamination than backscatter instruments. Forwardscatter instruments also have a much larger dynamic range, on the order of a factor of several thousand, as contrasted with the dynamic range of the transmissometer, which is twenty.

A major problem with the present commercially available forwardscatter visibility sensors is that calibration depends on the light source intensity. Therefore, a constant monitor for the output of light intensity is required. Dust on the optical system, which cannot be avoided for unattended field operation, is another source of error. Moreover, the large angle of forward scattering caused by the irregular shapes of snow also contaminates the visibility measurements. Furthermore, forwardscatter instruments for measuring visibility have not previously been practical due to the uncertainty of the relationship between the scattering of light and the extinction coefficient.

SUMMARY OF THE INVENTION

The present invention provides a reliable visibility sensor that operates on the principle of forwardscatter in combination with the weather identification system of the type described in U.S. Pat. No. 4,760,272. Unlike conventional forwardscatter visibility measurement instruments, the visibility sensor of the present invention is able to utilize signals from the weather identification portion of the system to neutralize many of the ambiguities that arise in the measurement of light transmission that are unrelated to visibility.

In one broad aspect the present invention represents an improvement to a weather identification system having a light beam source that transmits a partially coherent beam of light along a prescribed path, a first receiver positioned directly in the light beam path to produce signals in response to scintillations occurring in the beam of light, and signal processing means for producing a signal from the first receiver characteristic of rain and another signal from the first receiver characteristic of snow. The improvement of the invention resides in the provision of a second receiver obliquely positioned relative to the prescribed path to produce output signals responsive to forward scattering of light from scintillations occurring in the beam of light. The signal processing means is responsive to output signals from both the first and the second receiver to produce a signal characteristic of visibility in the ambient air through which the light beam travels.

In the present invention a single light source is shared by both the first receiver, which is employed to detect and identify precipitation, and the second or offbeam receiver which is employed to provide an indication of visibility. The light intensity detected by the second or offbeam receiver is normalized by the intensity detected by the first receiver or inbeam detector to obtain the forward scattering coefficient which is independent of the light source intensity. This system is therefore immune from fluctuation of the source intensity and from dust on the optical system.

In another broad aspect the invention may be considered to be a weather condition indicating system comprising: a partially coherent light beam generating transmitter arranged to transmit a partially coherent beam of light along a linear path, a first photosensitive receiver positioned directly in the path of the beam of light at a predetermined distance therefrom and in direct optical communication therewith, a first preamplifier circuit coupled to amplify signals from the first receiver generated in response to scintillations occurring in the light beam from the transmitter, a second photosensitive receiver positioned out of the path of the beam of light and at an acute angle relative thereto, a second preamplifier circuit coupled to amplify signals from the second receiver generated in response to forward scattering of weather particles in the beam, and a signal processor for separably isolating signals from the first receiver having frequency characteristics of rain and of snow and from the second receiver having a strength characteristic of visibility.

The improved weather identification system of the invention has several major optical electrical component assemblies. These are: an infrared transmitting module, a transmitter optical assembly, a receiver optical assembly, an automatic gain control normalizer, a signal processor, and a microprocessor unit.

One major concern of the system design is to ensure that the signal received by the receiver optical assembly maintains a high enough signal to noise ratio under various types of background light contamination. Such contamination is inevitably present to varying degrees due to sunshine, street lights and other sources. The infrared emitting diode is driven by a modulator to ensure that the system is immune to the background noise.

The infrared light emitted from the infrared emitting diode is collected by the transmitter optics to form a partially coherent light beam. This partially coherent light beam is pointed to the receiver optics which is located about 0.4 meters away. Particles falling through the beam will modulate the beam to induce light scintillation of the received signal. The receiver optical assembly employs a horizontal line aperture so as to be sensitive to the vertical motion of the precipitation.

The modulated light is detected by a first PIN photodiode followed by a first preamplifier and an automatic gain controlled (AGC) receiver. The AGC receiver acts as a normalizer to overcome the problems associated with power fluctuations caused by temperature change, component aging, dust on the lens and weather obscuring effects such as those produced by fog and haze. The output of the AGC receiver is demodulated and directed to the signal processor. Within the signal processor two major frequency bands of the scintillation spectrum are selected. Specifically, a high frequency band pass filter is employed to isolate signals in the one kilohertz to four kilohertz range, and a low frequency band pass filter is employed to isolate signals in the twenty five to two hundred fifty hertz range. The outputs of the high band pass filter and low band pass filter are used for quantitative rain and snow intensity measurements and an identification of the precipitation state. The signal of the high bandpass filter is proportional to the rain intensity, and the signal from the low bandpass filter is proportional to the snow intensity. The ratio of the high bandpass filter signal to the low bandpass filter signal is used to discriminate rain from snow.

To further increase the sensitivity of detecting a precipitation event, a particle counting channel is also used. The signal processor also provides a channel to monitor the carrier signal strength and to detect accidental blocking of the light beam or light source failure.

In the weather identification system of the invention a second receiver is positioned out of the path of the beam of partially coherent light and a an acute angle of alignment relative thereto. The second receiver has an optical section designed to collect the maximum amount of scattered light induced by fog, haze, or smoke. A second preamplification circuit is coupled to the second receiver to amplify the signals therefrom. These signals are then directed through a narrow band pass filter to reject the background noise.

The carrier signal as detected by the first receiver is then shifted in phase to match the output of the second receiver. The filtered signal from the second, off axis receiver, together with the phase shifted received carrier from the first receiver, are then fed into a synchronous detection stage to measure the average signal strength with a predetermined time constant, typically about ten seconds. The integrated output of the synchronous detection stage is then directed to a root mean square to direct current converter to produce a logarithmic output of signals from the second photosensitive receiver. This is done to increase the dynamic range of the signal level.

The invention may be described with greater clarity and particularity by reference to the accompanying drawings.

DESCRIPTION OF THE EMBODIMENT

Figure 1:
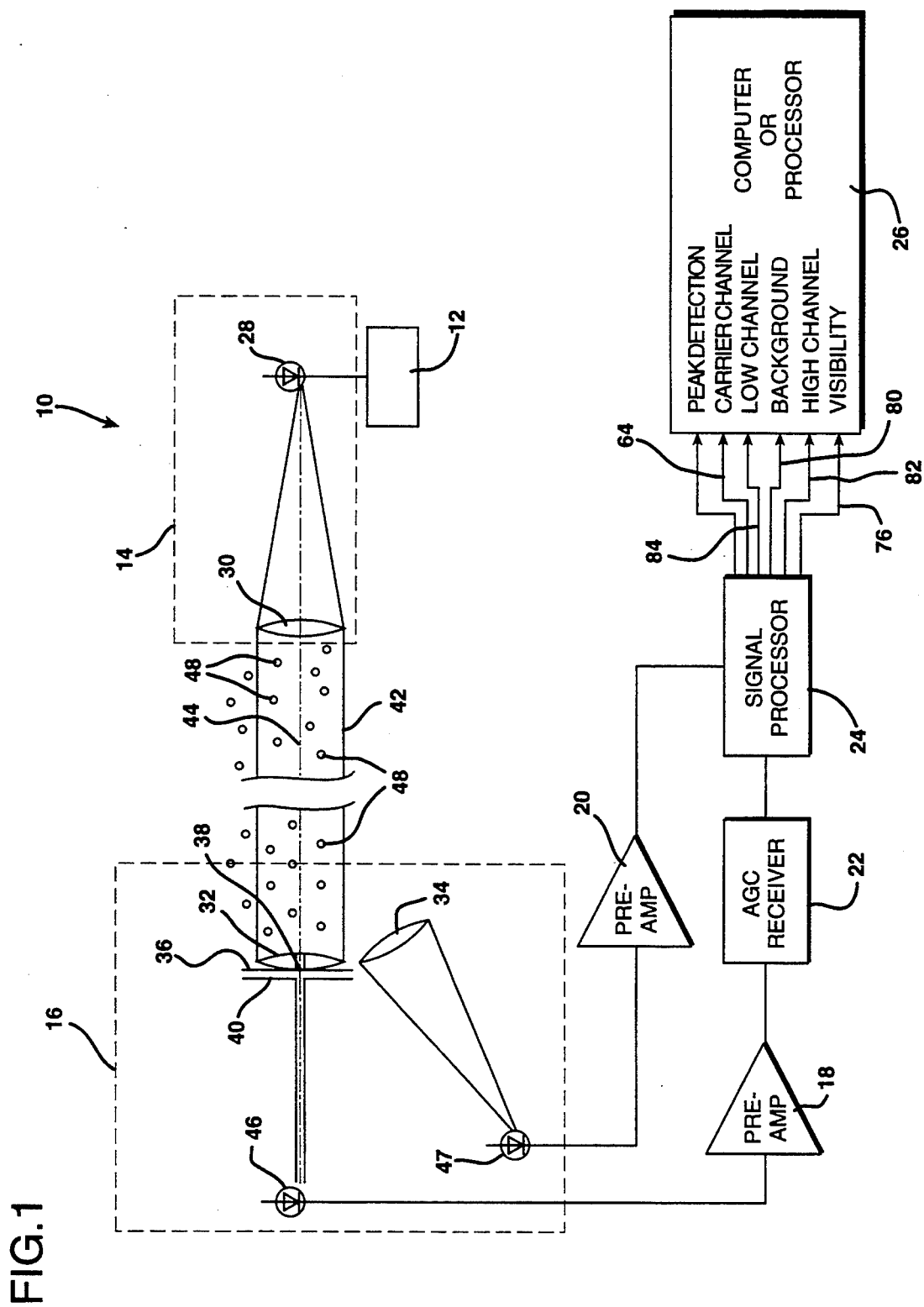
FIG. 1 is a functional block diagram of a preferred embodiment of the weather condition indicating system according to the invention.

FIG. 1 is a functional block diagram illustrating a weather identification system generally at 10 constructed according to the present invention. The weather identification system 10 includes an infrared (IRED) transmit modulator 12, a transmitter optical assembly 14, a receiver optical assembly 16, preamplification circuits 18 and 20, an AGC receiver 22, a signal processor 24, and a microprocessor unit 26.

The transmitter optical assembly employs an infrared light emitting diode 28 and a one hundred millimeter transmitter culminating lens 30. The carrier signal generator 12 is coupled to produce a carrier signal at about forty six kilohertz to drive the light beam transmitting IRED photo transmitting diode 28.

The receiver optical assembly 16 includes a first photosensitive receiver lens 32 having a focal length of one hundred millimeters and a second receiver lens with a focal length of 75 millimeters 34. The first receiver lens 32 employs a mask 36 which defines a horizontal slot 38 one millimeter in height and which is located directly behind the first receiver lens 32. An infrared filter 40 is located behind the mask 36.

The transmitter 14 produces a partially coherent light beam 42. The first photosensitive receiver lens 32 is located a predetermined distance, preferably 0.4 meters, from the transmitter optical assembly 14 that serves as the partially coherent light beam source. The first photosensitive receiver lens 32 is focused on a PIN photodiode 46. The PIN photodiode 46 produces electronic signals in response to scintillations caused by the movement of particles, indicated collectively at 48, that move between the light beam source 14 and the first photosensitive receiver lens 32. The electronic signals is then amplified by the preamplifier 18.

Figure 2:
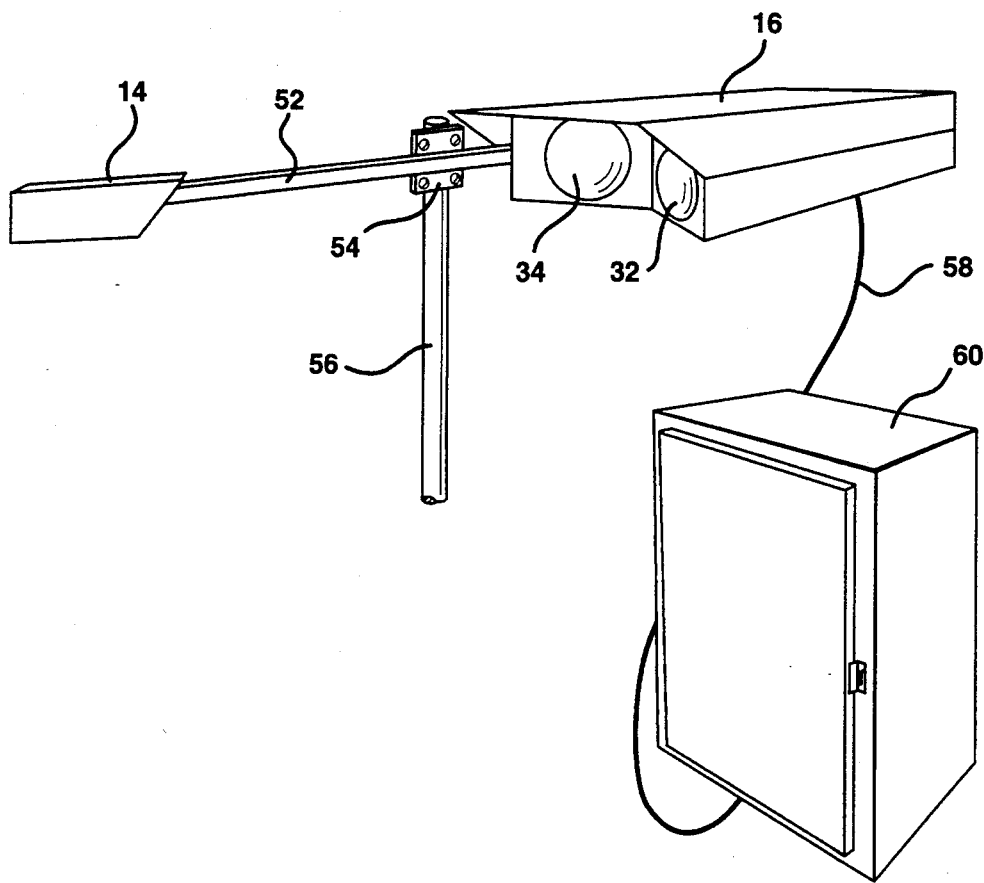
FIG. 2 is a perspective view illustrating the physical mounting and configuration of the optical components and the housing for the electronic components of the system of FIG. 1.
Figure 3:
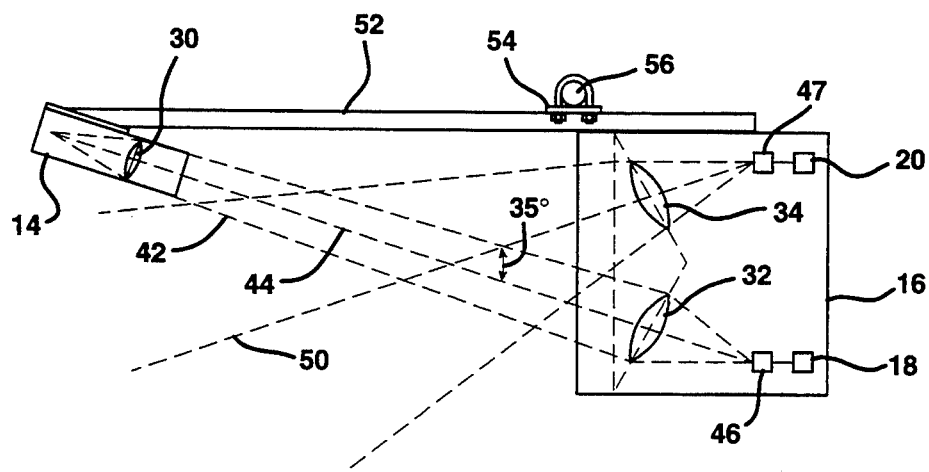
FIG. 3 is a diagrammatic top plan view illustrating the geometry of the optical components of FIG. 2.

As illustrated in FIGS. 2 and 3, the second photosensitive receiver lens 34 is located off axis or out of the path 44 of the light beam 42 obliquely and at an acute angle relative thereto. The second photosensitive receiver lens 34 is focused on a second PIN photodiode 47 that is identical to the photodiode 46. This signal of the PIN photodiode 47 is amplified by the preamplifier 20.

As shown in Fig. 3, the transmitter lens 30 is aligned to transmit the partially coherent beam of light 42 centered along a linear path indicated at 44. The center of the first photosensitive receiver lens 32 is aligned directly in the path 44 and in direct optical communication with the light beam 42 which focuses light on the PIN photodiode 46 that in turn produces electronic signals in response to scintillations caused by movement of the precipitation particles 48.

The second, offbeam photosensitive receiver lens 34 is aligned at an oblique, acute angle relative to the light beam path 44. The axis of alignment of the second lens 34 is indicated at 50 in FIG. 3. The linear axis 50 is oriented to intersect the path 44 of the light beam at an angle that may vary between about twenty five degrees and forty five degrees. Preferably, the axis of alignment 50 of the second photosensitive receiver lens 34 intersects the light beam path 44 at an acute angle of about thirty five degrees.

The physical configuration and arrangement of the optical components is illustrated in FIG. 2. The transmitter optical assembly 14 is laterally encased within a sensor head that is mounted on a horizontal beam 52 that is secured by a mounting bracket 54 to a vertical support mast 56. The receiver optical assembly 16 is likewise laterally enclosed. The first and second photosensitive receiver lenses 32 and 34, respectively, are level with each other and the receiver mask 36 is horizontal.

The transmitter optical assembly 14 and the receiver optical assembly 16 should be installed about six feet above the surrounding terrain, and the support mast 56 should be firmly embedded in the ground and should not sway or vibrate excessively in the wind. The mast 56 can be easily mounted on a tower or a cement platform. The receiver optical assembly 16 should be installed so that the axis of alignment 50 of the offbeam receiver lens 34 is preferably directed northward in the northern hemisphere so as to avoid any possible interference from the sun. The installation of other optical instruments nearby should be planned so that such instruments do not point directly at the receiver optical assembly 16.

Electrical signals and power are transmitted through conductors within a cable 58 to a weathertight electronic housing cabinet 60 that, contains the transmit modulator 12, the AGC receiver 22, the signal processor 24 and the microprocessor 26. The electronics cabinet 60 also includes power supplies and lightning protection devices. The casing 60 is a NEMA-4 rated weather proof enclosure.

The infrared transmitter modulator 12, the transmitter optical assembly 14, the first photosensitive receiver lens 32, the mask 36, the infrared filter 40, the PIN diode 46, the first preamplifier 18, the AGC receiver 22, and the portion of the signal processor 24 which processes signals from the AGC receiver 22 are fully described in U.S. Pat. No. 4,760,272, the disclosure of which is incorporated herein by reference. The novelty of the invention resides in the combination of a forward scattering visibility sensor with this prior system.

Figure 4:
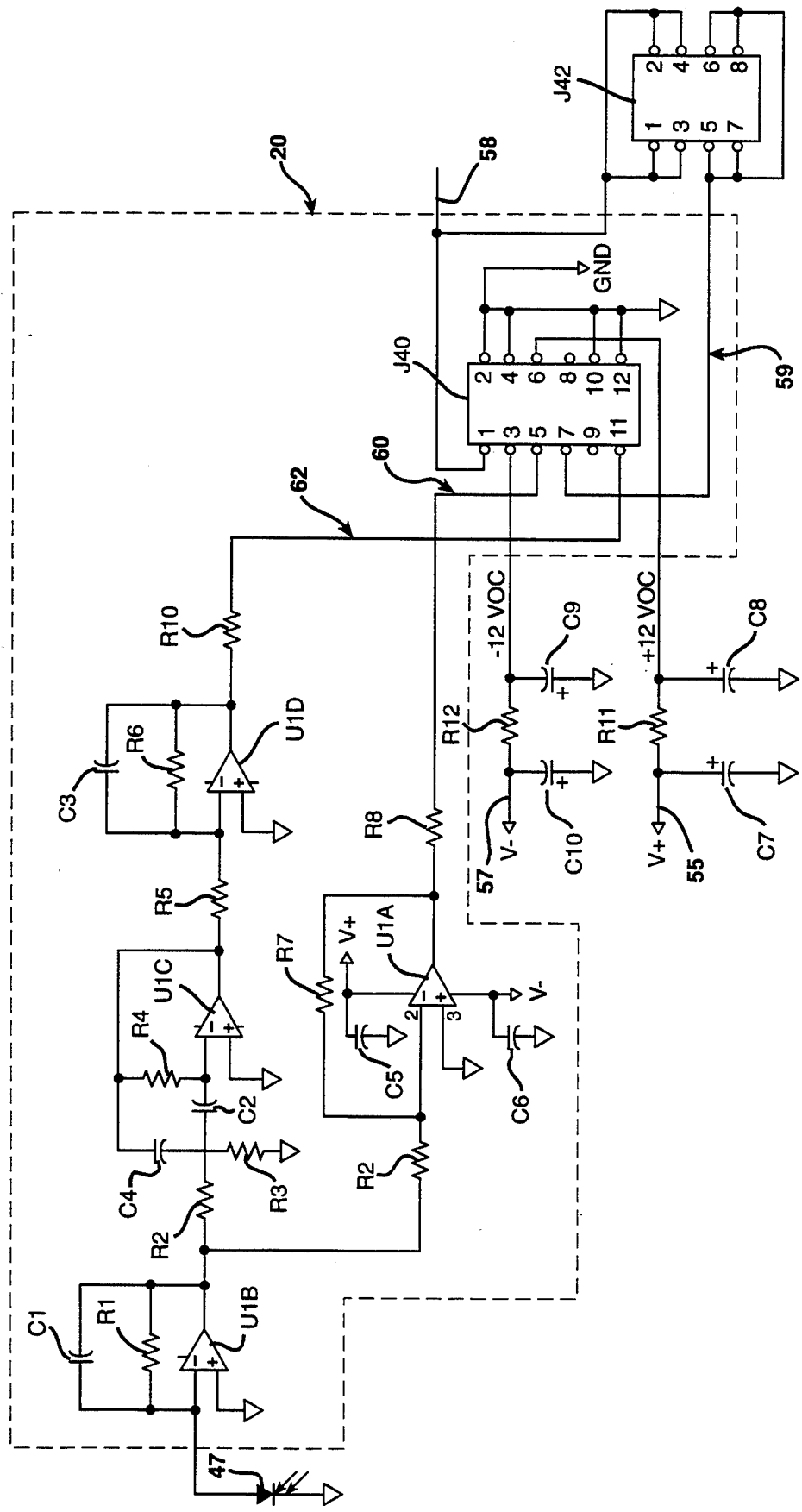
FIG. 4 is a schematic diagram illustrating the electronic components of the photosensitive receiver and preamplifier circuit employed to generate and amplify signals used to determine visibility.
Figure 5:
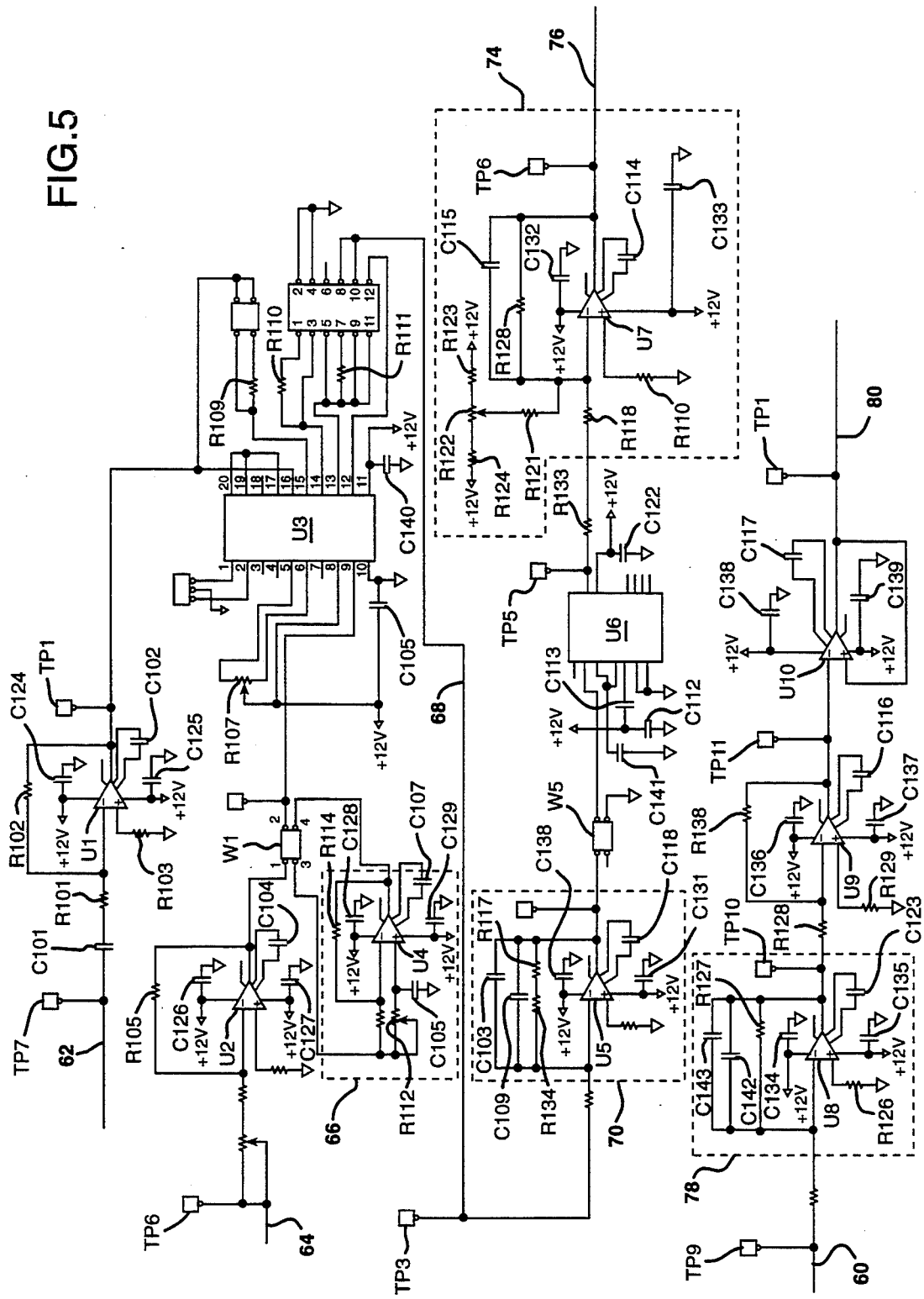
FIG. 5 is a schematic diagram illustrating the portion of the signal processor for isolating and processing signals from the photosensitive receiver of FIG. 4 to produce signals having a strength characteristic of visibility.

The electronic components utilized for the derivation of the output of the second off axis photosensitive receiver lens 34 are illustrated schematically in FIGS. 4 and 5. The suggested resistor and capacitor values for the circuit of FIG. 4 are set forth in Table 1 while those of FIG. 5 are set forth in Table 2. All of the amplifiers U1A, U1B, U1C and U1D in FIG. 4 are LF347N operational amplifiers, while all of the amplifiers U1, U2, U4, U5, U7, U8, U9 and U10 are LM101 operational amplifiers.

The PIN offbeam receiver photodiode 47 shown schematically in FIG. 4 is identical to the PIN inbeam receiver photodiode 46, both of which may be Litronix BPX61 PIN photodiodes, each of which has an active area of 2.7 millimeters square. The output of the photodetector 47 is directed to operational amplifier U1B which is the operative component of a current to voltage converter circuit that includes the capacitor C1 and resistor R1. The voltage signal from the output of amplifier U1B is passed as an input to amplifier U1C in a bandpass filter circuit. This band pass filter is centered at forty six kilohertz, which is the frequency of the carrier signal produced by the frequency modulating circuit or carrier signal generator 12, depicted in FIG. 1. The signal from the band pass filtering amplifier U1C is passed through resistor R5 as an input to a gain stage amplifier circuit employing an amplifier U1D. The output of amplifier U1D is directed as an input to pin 11 of a junction block J40.

The signal from the current to voltage converter amplifier U1B is also directed to an input of amplifier U1A in a direct current coupling circuit. This circuit measures the background light as detected by the photosensitive receiver lens 34. The output of amplifier U1A is indicative of the magnitude of background light and is transmitted as a input to pin 5 of junction block J40.

The preamplifier circuit 20 is supplied with positive twelve volt direct current power signal on line 55 and a negative twelve volt direct current signal on line 57. These power signals are filtered through resistor-capacitor networks as illustrated in FIG. 4 and appear as power inputs at pins 6 and 3 of the junction block J40, as shown.

The lens 34, like the lens 32, has a lens heater that is employed to evaporate moisture that might otherwise condense on it. To keep the transmitter and receiver lenses free of dew and frost, PTC thermistor heaters are bonded to the insides of these lenses. A thermistor is placed on each lens well below the central horizontal aperture area. The thermistors are continuously turned on during the operation of the weather condition indicating system. Power to the lens heater for the lens 34 is delivered through a lens heating junction block J42. The lens heating system operates on the fifteen volt direct current differential of power supplied on lines J8 and J9. This lens heating system is conventional and is described in U.S. Pat. No. 4,760.272, and is therefore not illustrated in FIG. 4.

The inputs from amplifiers U1A and U1D are respectively supplied to input pins 5 and 11 in junction block J40. The preamplified output signal from amplifier U1A appears on line 60, while that of amplifier U1D appears on line 62.

The signals on lines 60 and 62 from the preamplifier circuit 20 are then coupled to the signal processor 24. As previously noted, the signal processor 24 includes circuitry for processing the signals from the inbeam photosensitive receiver diode 46 as described in U.S. Pat. No. 4,760,272, and that portion of the circuitry is not repeated herein, but is incorporated by reference. However, the signal processor 24 also includes circuitry for processing the signals from the offbeam receiving photodiode 47. Specifically, the gain amplified signal on line 62 is connected to test point TP7, shown in FIG. 5, while the background light intensity signal on line 60 is connected to test point TP9 in Fig. 5. In addition, the signal processor 24 receives a signal from the AGC receiver 22 on line 64 at test point TP6 in FIG. 5.

The signal on line 62 from the second preamplifier circuit 20 is passed through amplifier U1 in a gain stage circuit. The amplified output from amplifier U1 is provided as an input to a demodulating circuit U3 at pin 17 thereof. Demodulated circuit U3 is an AD636 demodulation unit.

The signal 64 from the AGC receiver 22 is connected to a gain stage amplifier circuit as an input to amplifier U2. The output of the gain stage amplification circuit is connected as an input to pin 1 of connection block W1, the output at pin 3 of which is carried to amplifier U4 in a phase shifting circuit 66. The purpose of phase shifting circuit 66 is to synchronize the phases of signals from the first and second preamplifier circuits 18 and 20, which are respectively coupled to the first and second photosensitive receiver photodiodes 46 and 47. The phase shifting circuit 66 includes a resistor pot R112 which must be adjusted to match the phase of the signal on line 64 with the phase of the signal on line 62. The phase shifting circuit 66 adjusts the phase of the signal from the AGC receiver 22 on line 64 to synchronize the phase of that signal with the signal on line 62 from the preamplifier circuit 20. The output of the phase shifting 66 is coupled as an input at pin 4 and an output of pin 2 of the connecting strip W1 and coupled as an input on pin 5 to the demodulating circuit U3.

The demodulating circuit U3 demodulates the synchronized signals at pins 5 and 17 to remove the carrier frequency therefrom. The demodulator circuit U3 multiplies the signal at pin 5 from the first preamplifier circuit 18 and the signal at pin 17 from the preamplifier circuit 62 to produce a synchronized direct current output signal which is the product of those two inputs. This output signal appears on line 68 and is proportional to the ratio of the intensity of light received from the second photosensitive receiver lens 34 to that received from the first photosensitive receiver lens 32. The demodulator U3 ignores all signal components in the signals received on pins 5 and 17 except those components that are exactly in phase and at the same frequency, which is the carrier frequency of 46 kilohertz. The direct current output on line 68 is essentially a fully rectified sine wave where it appears at test point TP3.

The demodulator output on line 68 is then directed as an input to amplifier U5 in an integration circuit indicated generally at 70. The integration circuit 70 produces an output which is an average of the input on line 68 with respect to a predetermined time constant, which is preferably ten seconds.

The integrated output from the integration circuit 70 is directed through a connecting block W5 to a root mean square to direct current conversion circuit U6. The output of conversion circuit U6 is directed to amplifier U7 in a buffer amplifier circuit indicated generally at 74. The buffer amplifier circuit 74 has a resistor pot R122 which is used to shift the signal for calibration purposes. The output signal from the buffer amplifier circuit 74 appears at TP5 and as an output on line 76 to the microprocessor 26.

The output signal on line 76 has a strength characteristic of visibility, as derived from the second photosensitive receiver lens 34. The signal on line 76 has a magnitude proportional to the logarithm of the extinction coefficient. That is, it is proportional to the logarithm of the scattered light intensity. This signal is inversely proportional to the logarithm of visibility. The signal on line 76 is proportional to the quotient of one divided by the logarithm of visibility. By providing the signal as a logarithm, the dynamic range of the visibility sensor is greatly expanded.

The signal processor 24 also produces a background intensity signal from the input received from the preamplifier circuit 20 on line 60. The signal on line 60 appears at test point TP9 and is directed to an amplifier U8 in an integration circuit 78. The integration circuit 78, like the integration circuit 70, produces a direct current output signal at test point TP10 with respect to the same time constant of the integration circuit 70, which is ten seconds.

The integrated output from integration circuit 78 at test point TP10 is directed as an input to amplifier U9 of a gain amplification circuit, the output of which appears at test point TP11. The gain amplified signal from test point TP11 is directed as an input to an amplifier U10 of a buffer amplifier circuit, the output of which appears at test point TP12 and as an output on line 80 to the microprocessor 26. The output on line 80 is proportional to background light intensity. The signal on line 80 is employed to differentiate daytime and nighttime measurements.

Among other functions the microprocessor 26 corrects the raw visibility output on line 76 for rain and snow intensity. This correction is made on the basis of the signal from the first preamplifier circuit 18 on line 82 that is indicative of scintillations in the one to four kilohertz range, indicative of rain intensity, and on the basis of the signal on line 84 from the first preamplifier circuit 18 in the twenty five to two hundred fifty hertz range, which is indicative of snow intensity. The microprocessor 26 is formed of a single board containing an Intel MCS51 family controller, a 16 channel, 12 bit analog to digital converter section, memory, firmware, and a serial I/O section (RS-232C). The microprocessor 26 contains software for self testing, diagnostic analysis, a weather algorithm, and communications which allow the weather condition indicating system 10 to be used for remotely monitoring a site of interest.

The weather condition indicating system 10 constructed according to the invention is extremely reliable. False alarms of reports of precipitation when no precipitation exists occur at a rate of less than 0.2 percent, while a false identification rate in distinguishing rain from snow with some form of precipitation is less than one percent. The error in intensities of precipitation is less than five percent for precipitation of levels from 0.4 inches per hour to four inches per hour, and less than ten percent at precipitation levels of from 0.1 inch per hour to twenty inches per hour. Visibility can be determined from 0.001 miles to seven mile with less than twenty percent error.

Undoubtedly, numerous variations and modifications of the invention will become readily apparent to those familiar with conventional optical weather identification and measurement systems. For example, the signal from the second preamplifier circuit 20 can be phase adjusted to match that of the first preamplifier circuit, rather than the reverse situation in the embodiment described. Accordingly, the scope of the invention should not be construed as limited to this specific embodiment thereof depicted and described herein.

TABLE 1

| | |
|---|---|
| R1 | 221K ohms |
| R2 | 9.53K ohms |
| R3 | 1K ohms |
| R4 | 95.3K ohms |
| R5 | 4.02K ohms |
| R6 | 34.7K ohms |
| R7 | 10K ohms |
| R8 | 1.0K ohms |
| R9 | 10K ohms |
| R10 | 1.0K ohms |
| R11 | 2.7 ohms |
| R12 | 2.7 ohms |
| C1 | 5 picofarads |
| C2 | 330 picofarads |
| C3 | 47 picofarads |
| C4 | 330 picofarads |
| C5 | .1 microfarads |
| C6 | .1 microfarads |
| C7 | 100 microfarads |
| C8 | 100 microfarads |
| C9 | 100 microfarads |
| C10 | 100 microfarads |

TABLE 2

| | |
|---|---|
| R101 | 2.0K ohms |
| R102 | 100K ohms |
| R103 | 0 ohms |
| R104 | 5.0K ohms |
| R105 | 5.0K ohms |
| R106 | 5.0K ohms |
| R107 | 1.0K ohms |
| R109 | 5K ohms |
| R110 | 10K ohms |
| R111 | 10K ohms |
| R112 | 5.0K ohms |
| R113 | 5.0K ohms |
| R114 | 5.0K ohms |
| R115 | 100K ohms |
| R116 | 0 ohms |
| R117 | 8K ohms |
| R118 | 6.5K ohms |
| R119 | 0 ohms |
| R120 | 150K ohms |
| R121 | 221K ohms |
| R122 | 50K ohms |
| R123 | 95.0K ohms |
| R124 | 75.0K ohms |
| R125 | 221K ohms |
| R126 | 0 ohms |
| R127 | 221K ohms |
| R128 | 10K ohms |
| R129 | 0 ohms |
| R130 | 10K ohms |
| R131 | 2.2 ohms, 2W |
| R132 | 2.2 ohms, 2W |
| R133 | 150 ohms |
| R134 | 221K ohms |
| C101 | .01 microfarads |
| C102 | 15 picofarads |
| C103 | 1 microfarads |
| C104 | 15 picofarads |
| C105 | .1 microfarads |
| C107 | 15 picofarads |
| C108 | .041 microfarads |
| C109 | 47. microfarads |
| C110 | 150 picofarads |
| C112 | .1 microfarads |
| C113 | 10 microfarads |
| C114 | 100 picofarads |
| C115 | 1.0 microfarads |
| C117 | 100 picofarads |
| C118 | 100 microfarads |
| C119 | 100 microfarads |
| C120 | 100 microfarads |
| C121 | 100 microfarads |
| C122 | .1 microfarads |
| C123 | 150 picofarads |
| C124 | .1 microfarads |
| C125 | .1 microfarads |
| C126 | .1 microfarads |
| C127 | .1 microfarads |
| C128 | .1 microfarads |
| C129 | .1 microfarads |
| C130 | .1 microfarads |
| C131 | .1 microfarads |

TABLE 2-continued

| | |
|---|---|
| C132 | .1 microfarads |
| C133 | .1 microfarads |
| C134 | .1 microfarads |
| C135 | .1 microfarads |
| C137 | .1 microfarads |
| C138 | .1 microfarads |
| C139 | .1 microfarads |
| C140 | .1 microfarads |
| C142 | 1 microfarads |
| C143 | 47 microfarads |

I claim:

1. In a weather identification system having a light beam source that transmits a partially coherent beam of light along a prescribed path, a first receiver positioned directly in said light beam path to produce signals in response to scintillations occurring in said beam of light, and signal processing means for producing a signal from said first receiver characteristic of rain and another signal from said first receiver characteristic of snow, the improvement comprising a second receiver obliquely positioned relative to said prescribed path to produce output signals responsive to forward scattering of light from scintillations occurring in said beam of light and wherein said signal processing means has means for detecting a signal indicative of intensity of light received from said light beam by said first detector, means for detecting a signal indicative of light intensity of said forward scattering of light from said second receiver, and means for synchronizing said signal indicative of light intensity of said forward scattering of light and said signal indicative of intensity of light from said light beam to produce said signal characteristic of visibility, said signal processing means is responsive to output signals from both said first and said second receivers to produce a signal characteristic of visibility that is independent of intensity of said light source.

2. In a weather identification system having a light beam source that transmits a partially coherent beam of light along a prescribed path, a first receiver positioned directly in said light beam path to produce signals in response to scintillations occurring in said beam of light, and signal processing means for producing a signal from said first receiver characteristic of rain and another signal from said first receiver characteristic of snow, the improvement comprising: a carrier signal generator coupled to produce a carrier signal to drive said light beam source, a second receiver obliquely positioned relative to said prescribed path to produce output signals responsive to forward scattering of light from scintillations occurring in said beam of light and wherein said signal processing means is responsive to output signals from both said first and said second receivers to produce a signal characteristic of visibility and comprises synchronizing means coupled to receive said output signals from said second receiver and said carrier signal from said first receiver to produce a synchronized output in the form of a demodulated direct current signal proportional to the level of forward scattering occurring in said beam of light, integrating means for integrating said synchronized output with a predetermined time constant, and a root mean square to direct current converter circuit for producing said signal characteristic of visibility as a signal proportional to the logarithm of intensity of forward scattered light.

3. A weather condition indicating system comprising:
a partially coherent light beam generating transmitter arranged to transmit a partially coherent beam of light along a linear path,
a frequency modulating circuit for driving said partially coherent light beam generating transmitter with a carrier frequency,
a first photosensitive receiver positioned directly in said path of said beam of light at a predetermined distance therefrom and in direct optical communication therewith,
a first preamplifier circuit coupled to amplify signals from said first receiver generated in response to scintillations occurring in said light beam from said transmitter,
a second photosensitive receiver positioned out of the path of said beam of light and oriented at an acute angle relative thereto,
a second preamplifier circuit coupled to amplify signals from said second receiver generated in response to forward scattering of scintillations, and
a signal processor for separately isolating signals from said first receiver having frequency characteristics of rain and of snow and from said second receiver having a strength characteristic of visibility, and including a phase shifting circuit for synchronizing the phases of signals from said first and second preamplifier circuits, and a demodulating circuit coupled to said phase shifting circuit to demodulate synchronized signals from both said first and second preamplifier circuits to produce a synchronized direct current output signal proportional to the product of the intensity of light received from said second receiver to the intensity of light received from said first receiver in order to produce said signal from said second receiver having a strength characteristic of visibility.

4. A weather condition indicating system according to claim 3 wherein said signal processing means further comprises an integration circuit coupled to said demodulating circuit for integrating said synchronized direct current output signal with respect to a predetermined time constant, and a root mean square to direct current conversion circuit coupled to said integration circuit for producing said signal from said second receiver having a strength characteristic of visibility as the logarithm of the output of said integration circuit.

5. A weather identification system comprising:
a partially coherent light beam source, arranged to transmit a beam of light along a linear path,
a carrier signal generator coupled to drive said light beam source with a carrier signal,
a first photosensitive receiver positioned directly in said path of said beam of light a predetermined distance from said partially coherent light beam source and in direct optical communication therewith to produce electronic signals in response to scintillations caused by particle movement between said source and said first receiver,
a first preamplification circuit coupled to said first photosensitive receiver to produce an output indicative of said carrier signal input to said first photosensitive receiver,
a second photosensitive receiver positioned out of said path of said beam of light and oriented at an acute angle relative thereto to provide an output indicative of forward scattering of light from scintillations in said beam of light, a second preamplification circuit coupled to said second photosensitive receiver, a signal processing means coupled to both said first and second preamplification circuits for producing first, second and third outputs for detected scintillations wherein said first output has a frequency range above about one kilohertz characteristic of rain, said second output has a frequency range lower than that of said first output and characteristic of snow, and said third output has a signal strength characteristic of visibility and wherein said signal processing means is comprised of a phase shifting circuit coupled to said first preamplification circuit for adjusting the phase of said carrier signal input to said first photosensitive receiver to match the phase of said output from said second photosensitive receiver, a demodulation circuit coupled to said phase shifting circuit and to said second preamplifier circuit to produce a direct current signal indicative of said output from said second photosensitive receiver synchronized with said carrier signal output from said first preamplification circuit, and a root mean square to direct current converter coupled to said demodulation means to produce said signal characteristic of visibility as a direct current voltage directly proportional to the logarithm of intensity of forward scattering of scintillations detected by said second receiver and inversely proportional to the logarithm of visibility.

* * * * *